(12) United States Patent
Matsumoto

(10) Patent No.: US 6,779,890 B2
(45) Date of Patent: Aug. 24, 2004

(54) OPHTHALMIC PHOTOGRAPHIC APPARATUS

(75) Inventor: Kazuhiro Matsumoto, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/256,162

(22) Filed: Sep. 27, 2002

(65) Prior Publication Data

US 2003/0076477 A1 Apr. 24, 2003

(30) Foreign Application Priority Data

Oct. 22, 2001 (JP) .................................... 2001-323405

(51) Int. Cl.$^7$ ................................................ A61B 3/14
(52) U.S. Cl. .................................................... 351/206
(58) Field of Search ................................ 351/205, 206, 351/208, 211, 212, 221

(56) References Cited

U.S. PATENT DOCUMENTS

| 4,252,420 A | * | 2/1981 | Kohayakawa | ............... 351/208 |
| 4,820,037 A | | 4/1989 | Kohayakawa et al. | ...... 351/211 |
| 4,848,896 A | | 7/1989 | Matsumoto | .................. 351/211 |
| 4,952,049 A | | 8/1990 | Matsumoto | .................. 351/211 |
| 4,991,584 A | * | 2/1991 | Kobayashi et al. | .......... 600/401 |
| 5,233,372 A | | 8/1993 | Matsumoto | .................. 351/221 |
| 5,455,644 A | | 10/1995 | Yazawa et al. | .............. 351/206 |
| 5,847,805 A | | 12/1998 | Kohayakawa et al. | ...... 351/210 |
| 6,158,864 A | | 12/2000 | Masuda et al. | ............. 351/206 |
| 6,273,565 B1 | | 8/2001 | Matsumoto | .................. 351/210 |
| 6,327,375 B1 | | 12/2001 | Matsumoto et al. | ......... 382/117 |
| 6,456,787 B1 | | 9/2002 | Matsumoto et al. | ........... 396/18 |

* cited by examiner

Primary Examiner—George Manuel
(74) Attorney, Agent, or Firm—Fitzpatrick, Cella, Harper & Scinto

(57) ABSTRACT

An ophthalmic photographic apparatus determines whether an eye under examination is the left eye or the right eye. In accordance with the determination, a corresponding fixation target is presented to a main unit, and a reference mark corresponding to the eye under examination, which is stored in a memory, is displayed on a monitor. An alignment mark projected onto and reflected from the anterior eye portion and the reference mark are displayed on the monitor, and hence alignment appropriate for the left and right eyes can be performed.

21 Claims, 5 Drawing Sheets

OPHTHALMIC PHOTOGRAPHIC APPARATUS

BACKGROUND OF THE INVENTION

1. Field of the Invention

The present invention relates to ophthalmic photographic apparatuses for use in ophthalmic hospitals.

2. Description of the Related Art

In order to align a subject's eye (eye under examination) and a photographic apparatus, a fundus camera projects marks so that an image reflected from the cornea can be formed substantially conjugate to the fundus of the eye. The image reflected from the cornea and an image of the fundus are displayed on a monitor and are observed. The fundus camera is positioned so that the image reflected from the cornea can be in focus and be displayed symmetrically relative to the center of the monitor.

In the foregoing known example, the following problems occur:

(1) In general, fundus photography in group examination is performed by aligning the approximate central point between the optic disk (discus nervi optici) and the macula lutea to be at the center of the photographic screen. Since the field angles of the optic disk and the macula lutea are separated from each other by approximately 18 degrees, this photographic method captures images with a tilt of approximately 9 degrees.

The eyeball optical system has rotation symmetry with respect to the optical axis between the approximate center of the pupil and the macula lutea. Capturing an image eccentrically means that the image is captured while decentering the eyeball. As a result, one side of the image tends to become flared. When a visual field diaphragm is reduced to avoid flare, the photographic field angle becomes narrow.

(2) In the known method, images are captured from an eccentric position relative to the center of the pupil. When capturing an image of a subject's eye having the pupil with a small diameter, the fundus of the eye cannot be illuminated uniformly.

SUMMARY OF THE INVENTION

In order to solve the foregoing problems, it is an object of the present invention to provide an ophthalmic photographic apparatus for appropriately displaying fixation targets corresponding to a subject's left and right eyes under examination.

In order to achieve the foregoing objects, according to the present invention, an ophthalmic photographic apparatus is provided including a mark projecting unit for projecting a mark onto a cornea of an eye under examination; an observation unit for observing a reflected image of the mark and an image of a fundus of the eye; a left-right detecting unit for detecting whether the eye under examination is the left eye or the right eye; and a control unit for displaying, on the observation unit, the reference mark for aligning the reflected image of the mark at different positions corresponding to the left and right eyes in accordance with information detected by the left-right detecting unit.

As described above, an ophthalmic photographic apparatus according to the present invention includes a determination unit for determining whether a subject's eye (eye under examination) is the left eye or the right eye, and reference marks for alignment are presented at eccentric positions in accordance with the determination. Thus, the following advantages can be achieved:

(a) Since flare-free, satisfactory images can be obtained, the image capturing and reading efficiency can be improved;
(b) With tolerance to flare, images can be simultaneously taken at wide field angles, and the diagnosis efficiency can be further improved; and
(c) Since images can be taken from the center of the pupil, satisfactory images of the fundus of a subject's eye having a small-diameter pupil can be captured.

Further objects, features, and advantages of the present invention will become apparent from the following description of the preferred embodiments with reference to the attached drawings.

DESCRIPTION OF THE PREFERRED EMBODIMENT

Figure 1:
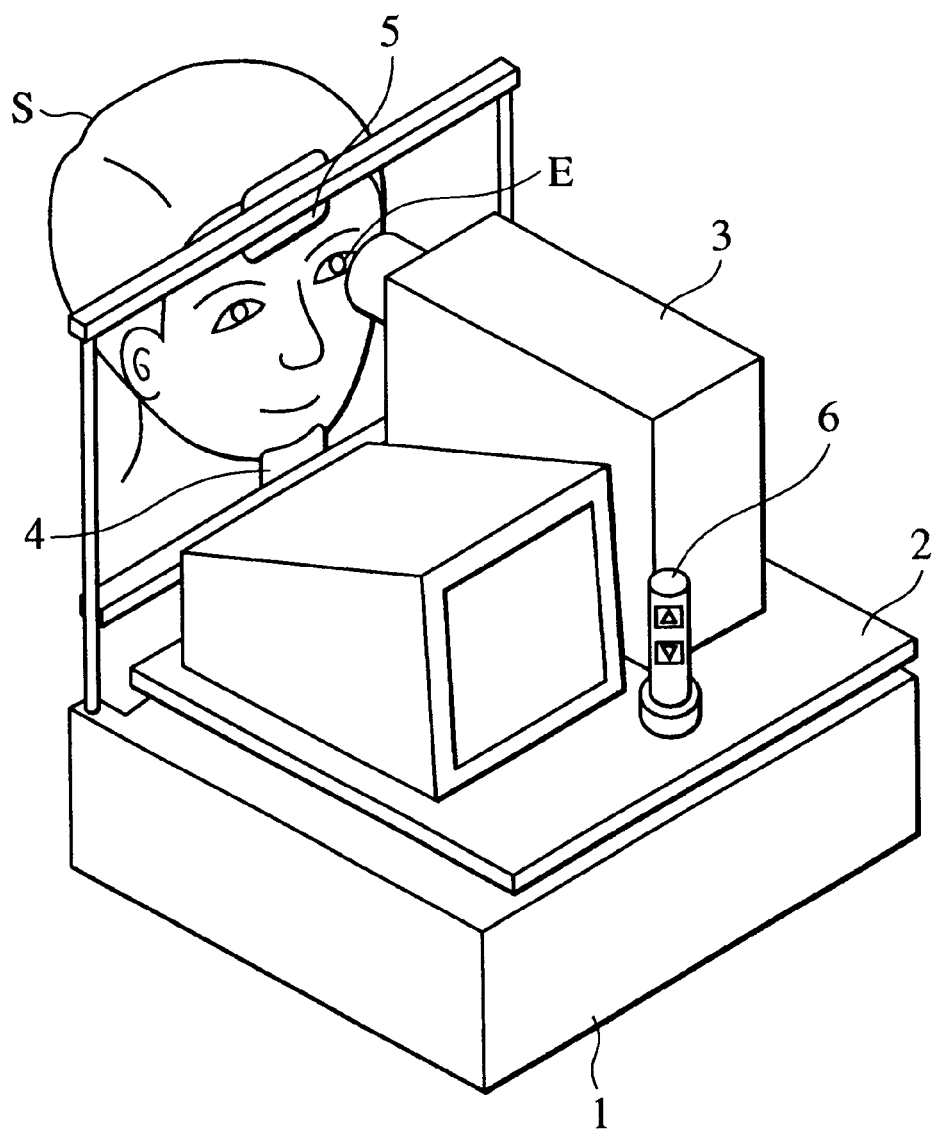
FIG. 1 is an external perspective view of a fundus camera according to an embodiment of the present invention.

The present invention will become clear from the following description of the preferred embodiment with reference to the accompanying drawings. FIG. 1 is an external view of a fundus camera. On a base 1 containing a circuit board and electrical components, a stage 2 is mounted in a horizontally movable manner. On the stage 2, a main unit 3 is mounted in a vertically movable manner. On the base 1, a chinrest 4 for holding the chin of a subject S and a headrest 5 are provided. An examiner who wants to take a photograph operates a joystick 6, which is provided on the stage 2, to adjust the positional relationship between the main unit 3 and the subject's eye E.

Figure 2:
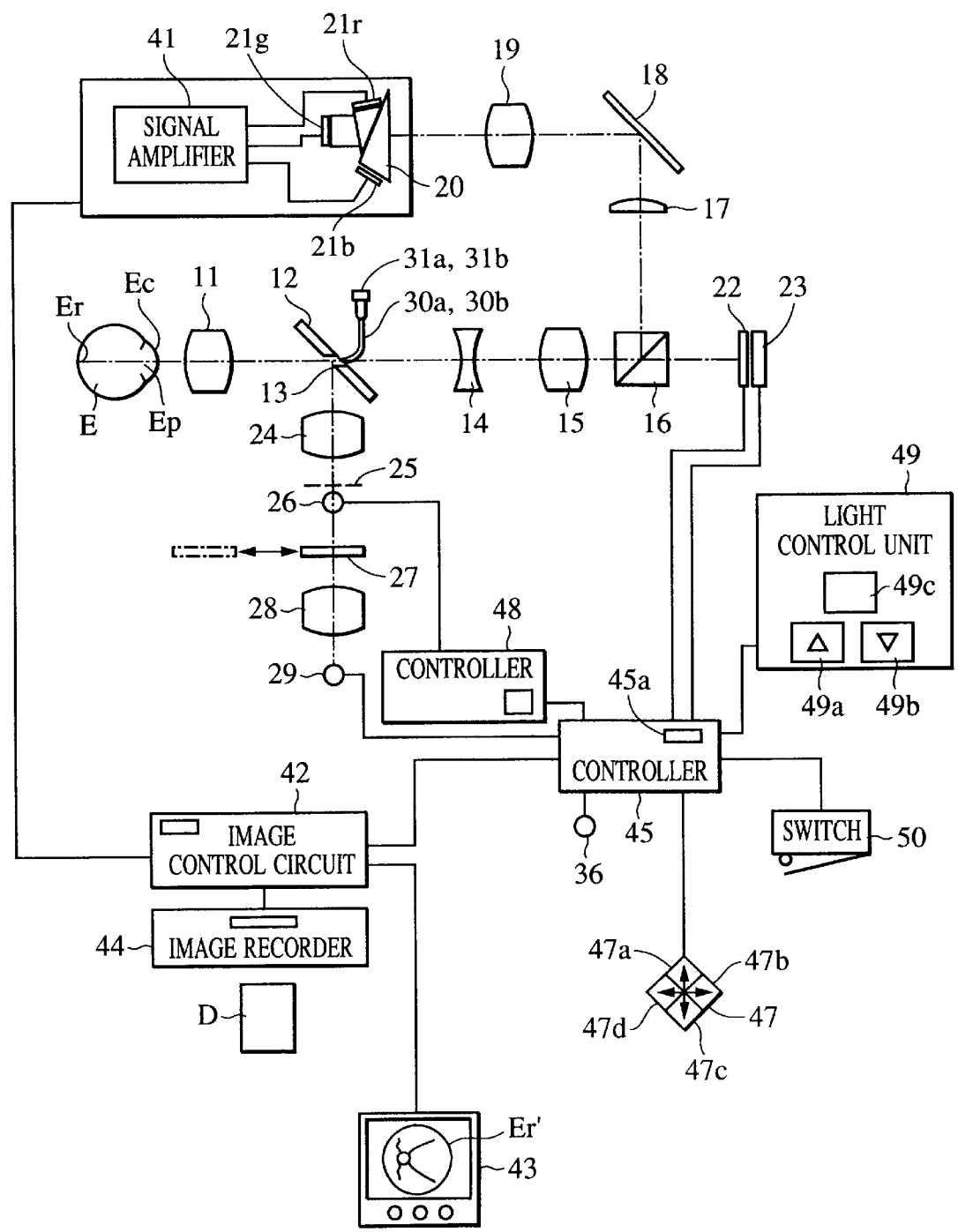
FIG. 2 is a schematic diagram of the optical system and the electrical system.

FIG. 2 is a diagram of the optical system and the electrical system in the fundus camera 3. In front of the subject's eye E, an objective lens 11, an apertured mirror 12, a photographic diaphragm 13 disposed in the aperture of the apertured mirror 12, a focus lens 14 which is movable along the optical axis, a photographic lens 15, and an optical-path branching prism 16 are sequentially disposed. In the reflecting direction of the optical-path branching prism 16, a lens 17, a mirror 18, a lens 19, a color separation prism 20, and image pickup elements 21r, 21b, and 21g are provided. The color separation prism 20 directs infrared light and red light toward the image pickup element 21r, blue light toward the image pickup element 21b, and green light toward the image pickup element 21g, thus forming a fundus photographing unit.

In the transmission direction of the optical-path branching prism 16, a liquid crystal display (LCD) 22 functioning as an internal fixation target and a backlight unit 23 are disposed to form an internal fixation target presenting unit.

In the incident direction of the apertured mirror 12, a relay lens 24, a diaphragm 25 having a ring aperture, a stroboscopic light source 26 for emitting flashes, a wavelength selection filter 27 for blocking visible light and transmitting infrared light, which can be freely inserted into and removed from the optical path, a condenser lens 28, and an observation light source 29, such as a halogen lamp, for emitting fixed light including visible light and infrared light, are disposed. These components, together with the apertured mirror 12 and the objective lens 11, form a fundus illuminator.

On both sides of the photographic diaphragm 13, end faces of fibers 30a and 30b are disposed. Light sources 31a and 31b are disposed on an end face opposite to the photographic diaphragm 13. The end face at which the photographic diaphragm 13 is provided functions as a mark for adjusting the working distance. The mark is disposed at a position at which an image reflected from the cornea can be substantially conjugate to the fundus Er when the distance between the objective lens 11 and the cornea of the subject's eye E is appropriate.

The outputs of the image pickup elements 21r, 21b, and 21g are connected to an image control circuit 42 via a signal amplifier circuit 41 for amplifying electrical signals. A television monitor 43, an image recorder 44, and a controller 45 with a memory 45a are connected to the image control circuit 42. The image recorder 44 is a drive for writing images to and reading images from a recording medium D, such as an MO (magneto-optical disk), an MD (mini disk), a DVD-RAM (digital versatile disk-random access memory), a VCR (videocassette recorder) tape, or a hard disk, which can store and maintain information without an external power supply. The LCD 22, the observation light source 29, a photographic switch 36, an operation unit 47 for specifying the position at which the fixation target is presented, a stroboscopic flash controller 48 for controlling the stroboscopic light source 26, a light control unit 49 for controlling the light intensity of the observation light, the light control unit 49 including switches 49a and 49b and a display unit 49c, and a detector switch 50 for detecting the position of the main unit 3, are connected to the controller 45.

In the LCD 22, cells which can control the transmission and blocking of light are arranged in the form of matrix. The LCD 22 functions as a fixation target when the backlight unit 23 is observed through a light transmitting portion of the LCD 22. The backlight unit 23 includes a plurality of LEDs (light emitting diodes). The position of the light transmitting portion of the LCD 22, that is, the fixation target, is controlled by the operation unit 47 for specifying the position at which the fixation target is presented. In other words, the examiner who wants to take a photograph operates four switches 47a, 47b, 47c, and 47d of the operation unit 47 to lead the subject's visual axis to an arbitrary position. The light transmitting portion of the LCD 22 is presented at a position where the center of the line between the optical disk and the macula lutea becomes substantially the center of the screen when the subject's eye E is fixed on the fixation target.

It is assumed that the subject's eye E under examination is the left eye and a photograph is taken using the fundus camera. The examiner who wants to take a photograph asks the subject S to sit in front of the fundus camera and to position his or her chin on the chinrest 4 and his or her forehead against the headrest 5. The examiner operates the joystick 6 to position the main unit 3 in front of the subject's eye E.

Figure 3:
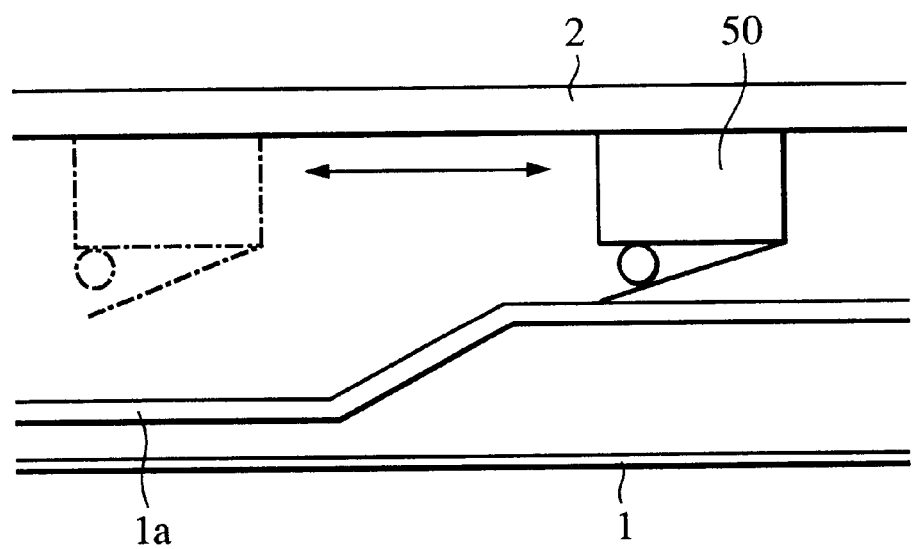
FIG. 3 is schematically illustrates a position detector.

FIG. 3 shows a position detector. The height of an upper portion 1a of the base 1 differs in the horizontal direction. Due to the difference in height, the detector switch 50 is turned on and off. Thus, it is possible to detect the position of the main unit 3, that is, it is possible to detect whether the main unit is at the left or at the light, and hence it can be detected whether the subject's eye E is the left eye or the right eye. In other words, when the controller 45 detects, for example, that the main unit 3 is at the position of the left eye using the detector switch 50, the controller 45 presents a fixation target for capturing an image of the left eye.

When the examiner observes the subject's eye E, a light beam emitted from the observation light source 29 is focused by the condenser lens 28, and the wavelength selection filter 27 disposed in the optical path only transmits infrared light. The transmitted light passes through the stroboscopic light source 26, the diaphragm 25, and the relay lens 24, and the light is reflected to the left by the peripheral mirror portion of the apertured mirror 12. The reflected light passes through the objective lens 11 and the pupil Ep of the subject's eye E and illuminates the fundus Er.

An image of the fundus Er, which is illuminated by infrared light, again passes through the objective lens 11, the photographic diaphragm 13, the focus lens 14, and the photographic lens 15 and is reflected upward by the optical-path branching prism 16. The reflected image passes through the lens 17 and is reflected to the left by the mirror 18, and the reflected image enters the color separation prism 20 through the lens 19. The image is formed at the image pickup element 21r for the red and infrared light and is converted into an electrical signal. The signal passes through the signal amplifier circuit 41 and is amplified by a predetermined factor. The amplified signal is input to the image control circuit 42 and displayed on the television monitor 43.

Figure 4:
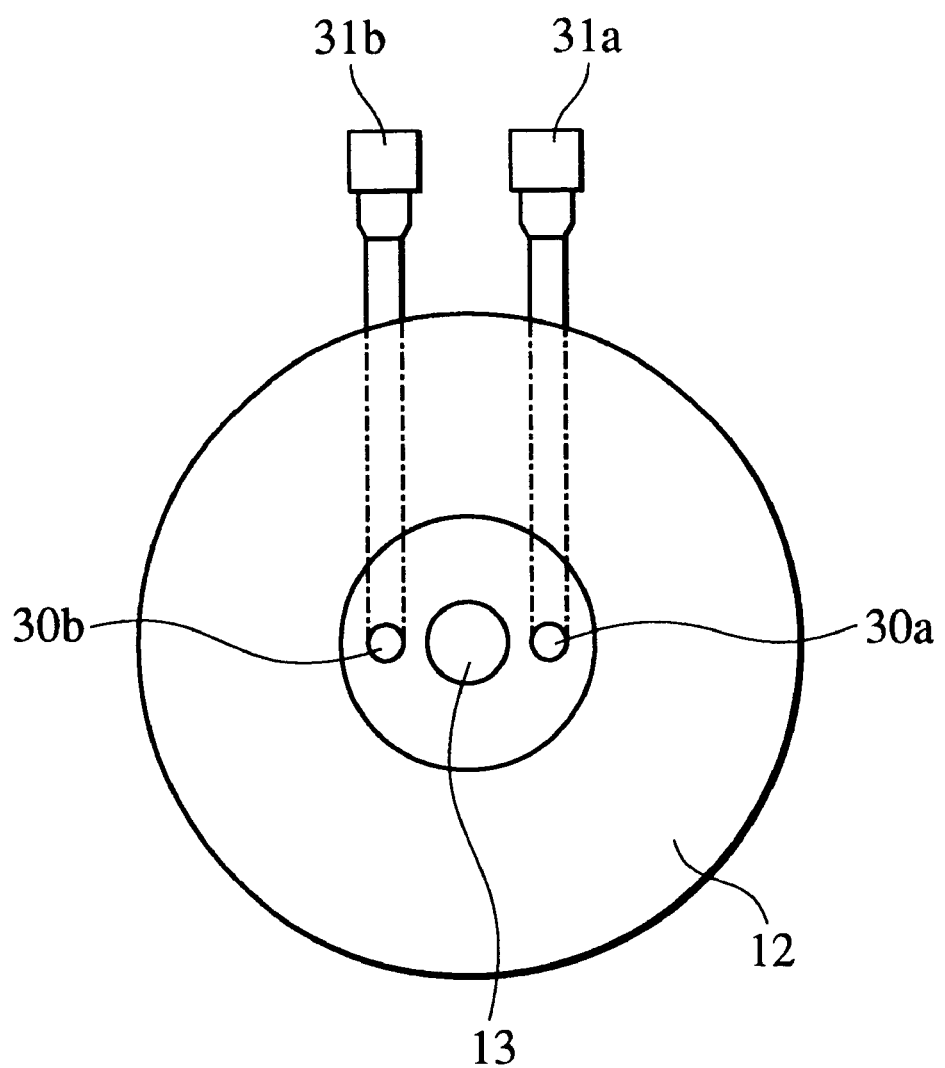
FIG. 4 schematically illustrates the arrangement of an apertured mirror, fibers, and light sources.

FIG. 4 illustrates the apertured mirror 12 viewed from the objective lens 11. Light emitted from the light sources 31a and 31b enters the fibers 30a and 30b, and the end face at which the photographic diaphragm 13 is provided is illuminated with this light. An image of this end face is formed by the objective lens 11 substantially at the midpoint between the apex of the cornea Ec of the subject's eye E and the center of the corneal curvature. If the working distance between the subject's eye E and the objective lens 11 is appropriate, an image of the marks reflected from the cornea, which is formed by the fibers 30a and 30b, is formed substantially conjugate to the fundus Er. In other words, the image reflected from the cornea passes through the objective lens 11, the photographic diaphragm 13, the focus lens 14, and the photographic lens 15 and is reflected upward by the optical-path branching prism 16. The reflected image is formed in the vicinity of the lens 17, and the image is reflected to the left by the mirror 18. Similar to the image of the fundus, this image reflected from the cornea is formed at the image pickup element 21r through the lens 19.

Figure 5A:
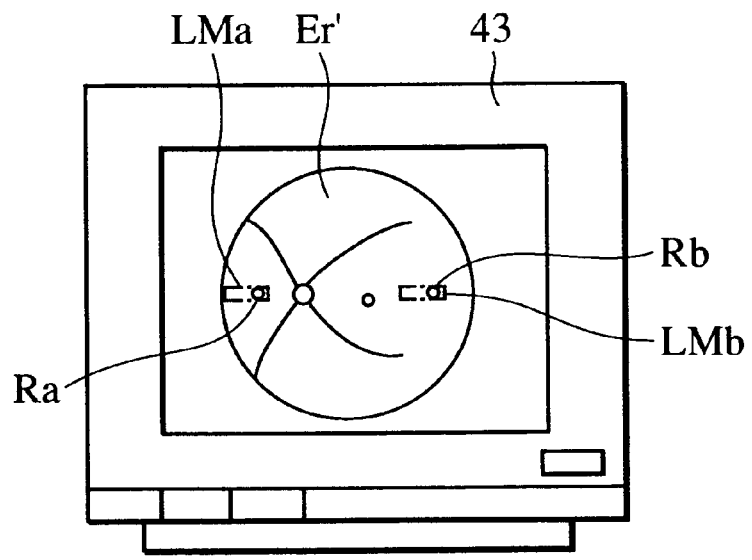
FIGS. 5A and 5B are illustrations of images of the fundus and fixation targets displayed on a television monitor.

FIG. 5A shows an image of the fundus (fundus image) Er' in which reflected images Ra and Rb, formed by the cornea Ec, of the marks are displayed on the television monitor 43. The controller 45 displays reference marks LMa and LMb for alignment, which are stored in the memory 45a and which are used to take a photograph of the left eye on the television monitor 43. The center of the reference marks LMa and LMb is decentered to the right with respect to the center of the fundus image Er' by approximately six degrees. Having observed the fundus image Er' and the images reflected from the cornea Ra and Rb, the examiner operates the joystick 6 so that the reflected images Ra and Rb are placed inside the reference marks LMa and LMb and the contrast of the reflected images Ra and Rb is maximized. After confirming that the photographic range, positions, and focusing are satisfactory, the examiner operates the photographic switch 36 and captures a still image.

The controller 45 detects that the photographic switch 36 is operated and emits light from the stroboscopic light source 26 via the stroboscopic flash controller 48. The light emitted from the stroboscopic light source 26 passes through the ring aperture of the diaphragm 25 and the relay lens 24 and is reflected to the left by the peripheral mirror portion of the apertured mirror 12. The reflected light passes through the objective lens 11 and the pupil Ep of the subject's eye E, and the fundus Er is illuminated with this light.

The illuminated fundus image Er' again passes through the objective lens 11, the photographic diaphragm 13, the focus lens 14, and the photographic lens 15, and the image Er' is reflected upward by the optical-path branching prism 16, which is disposed in the optical path. The reflected image Er' passes through the lens 17 and is reflected to the left by the mirror 18. The image Er' passes through the lens 19 and enters the color separation prism 20. The image is formed at the image pickup elements 21r, 21b, and 21gb and converted into an electrical signal. The signal is amplified by the signal amplifier circuit 41 by a predetermined factor, and the amplified signal is input to the image control circuit 42. Using the amplified signal and presentation position information for the fixation target, the image recorder 44 records a color fundus image in the recording medium D, and the recorded image is displayed on the television monitor 43.

Figure 5B:
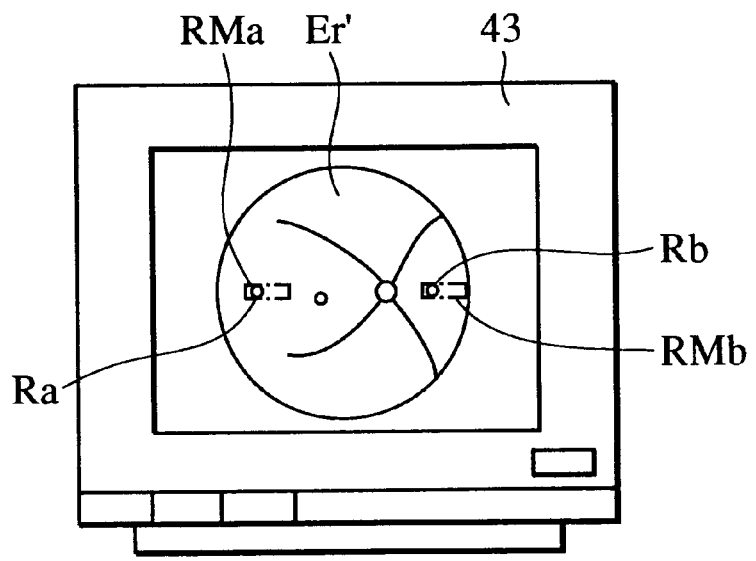

In order to capture an image when the subject's eye E under examination is the right eye, the examiner operates the joystick 6 and moves the main unit 3 including the optical system to be in front of the right eye. Accordingly, the detector switch 50 for detecting whether the left eye or the right eye is to be examined is turned off. Having detected that the detector switch 50 has been turned off, the controller 45 presents a fixation target for the right eye and displays reference marks RMa and RMb for right-eye alignment, which are stored in the memory 45a, on the television monitor 43. As shown in FIG. 5B, the center of the reference marks RMa and RMb is decentered to the left with respect to the center of the fundus image Er by approximately six degrees.

As described above, the fundus Er is illuminated with infrared light emitted from the observation light source 29. The illuminated fundus image Er' and the reflected images of the marks Ra and Rb, which are formed by illuminating the cornea Ec by the light sources 31a and 31b, are displayed on the television monitor 43. As described above with reference to FIG. 5B, the examiner operates the joystick 6 to position the main unit 3 in accordance with the subject's eye E so that the reflected images Ra and Rb can be symmetrically placed inside the reference marks RMa and RMb and the contrast of the reflected images Ra and Rb can be maximized.

After confirming that the photographic range, positions, and focusing are satisfactory, the examiner operates the photographic switch 36 and captures a still image. Having detected that the photographic switch 36 is operated, the controller 45 controls the stroboscopic light source 26 to emit light so that the fundus Er can be illuminated with visible light. The illuminated fundus image Er' again passes through the objective lens 11, the photographic diaphragm 13, the focus lens 14, and the photographic lens 15 and is reflected upward by the optical-path branching prism 16. The reflected light passes through the lens 17 and is reflected to the left by the mirror 18. The reflected light enters the color separation prism 20, and an image is formed at the image pickup elements 21r, 21b, and 21b. The image is converted into an electrical signal, and the electrical signal is amplified by the signal amplifier circuit 41 by a predetermined factor. The amplified signal passes through the image control circuit 42 and is recorded by the image recorder 44 as a color fundus image in the recording medium D. The image is displayed on the television monitor 44, and the image capturing process is terminated.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An ophthalmic photographic apparatus comprising:

illumination means for illuminating a fundus of an eye to be examined;

image capturing means for capturing an image of the fundus illuminated by the illumination means;

guiding means for guiding the line of view of the eye to be examined;

mark projecting means for projecting a mark for alignment onto a cornea of the eye to be examined;

a reference mark for permitting a reflected image of the mark to be aligned therewith;

observation means for observing the reflected image of the mark and the reference mark along with the image of the fundus of the eye to be examined;

left-right detecting means for detecting whether the eye to be examined is the left eye or the right eye; and control means for displaying the position of the reference mark on the observation means in accordance with information detected by the left-right detecting means.

2. An ophthalmic photographic apparatus according to claim 1, further comprising a base, a moving portion, and an operation member for moving the position of the moving portion.

3. An ophthalmic photographic apparatus according to claim 2, wherein the left-right detecting means detects whether the eye to be examined is the left eye or the right eye by detecting the relational positions of the base and the moving portion.

4. An ophthalmic photographic apparatus according to claim 1, further comprising storage means for storing data representing the position at which the reference mark corresponding to the left eye or the right eye is displayed.

5. An ophthalmic photographic apparatus according to claim 1, wherein the guiding means comprises fixation target presenting means for presenting a fixation target to the eye to be examined, wherein the position at which the fixation target is presented to the eye to be examined is changed in accordance with the information detected by the left-right detecting means.

6. An ophthalmic photographic apparatus according to claim 1, wherein the guiding means comprises fixation target presenting means for presenting a fixation target to the eye to be examined, and further comprising fixation target operating means for adjusting the position of the fixation target.

7. An apparatus comprising:

mark projecting means for projecting a mark for alignment onto a cornea of an eye to be examined;

a reference mark for permitting a reflected image of the mark to be positioned relative thereto;

left-right detecting means for detecting whether the eye to be examined is the left eye or the right eye;

display means for displaying the mark for alignment and the reference mark; and control means for changing the position at which the reference mark is displayed in accordance with a detection result obtained by the left-right detecting means.

8. An ophthalmic photographic apparatus comprising:

an illuminator configured and positioned to illuminate a fundus of an eye to be examined;

an image recorder configured and positioned to perform image capturing for capturing an image of the fundus illuminated by the illuminator;

a display configured and positioned to present a fixation target to the eye to be examined for guiding the line of view of the eye to be examined;

a mark projector configured and positioned to project a mark for alignment onto a cornea of the eye to be examined;

a reference mark for permitting a reflected image of the mark to be aligned therewith;

an observation device configured and positioned to permit a user to observe the reflected image of the mark and the reference mark along with the image of the fundus of the eye to be examined;

a position detector configured and positioned to detect whether the eye to be examined is the left eye or the right eye; and a controller, connected to the observation device and configured and positioned to control the observation device to position and display the reference mark in accordance with information detected by the position detector.

9. An ophthalmic photographic apparatus according to claim 8, further comprising a base, a moving portion, and an operation member, connected to the moving portion and configured and positioned to move the position of the moving portion.

10. An ophthalmic photographic apparatus according to claim 9, wherein the position detector detects whether the eye to be examined is the left eye or the right eye by detecting the relational positions of the base and the moving portion.

11. An ophthalmic photographic apparatus according to claim 8, further comprising a memory storing data representing the position at which the reference mark corresponding to the left eye or the right eye is displayed.

12. An ophthalmic photographic apparatus according to claim 8, wherein the position at which the display presents the fixation target to the eye to be examined is changed in accordance with the information detected by the position detector.

13. An ophthalmic photographic apparatus according to claim 8, further comprising a fixation target operating device connected to the display and configured and positioned to adjust the position of the fixation target.

14. An apparatus comprising:

a mark projector configured and positioned to project a mark for alignment onto a cornea of an eye to be examined;

a display configured and positioned to display a reference mark for permitting a reflected image of the mark to be aligned therewith;

a position detector configured and positioned to detect whether the eye to be examined is the left eye or the right eye; and a controller configured and positioned to control the display to change the position at which the reference mark is displayed in accordance with a detection result obtained by the position detector.

15. A method of photographing the fundus of an eye, comprising the steps of:

illuminating a fundus of an eye to be examined;

guiding the line of view of the eye to be examined by presenting a fixed target to the eye to be examined;

projecting a mark for alignment onto a cornea of the eye to be examined;

displaying a reference mark for permitting a reflected image of the mark to be aligned therewith and displaying the reflected image of the mark along with the image of the fundus of the eye to be examined;

detecting whether the eye to be examined is the left eye or the right eye;

displaying the position of the reference mark in said displaying step in accordance with information detected by said detecting step; and performing image capturing for capturing an image of the fundus illuminated in said illuminating step.

16. A method according to claim 15, further comprising the step of moving the position of a moving portion to which means for performing said illuminating, guiding, projecting, displaying, detecting, and performing are connected.

17. A method according to claim 16, wherein said detecting step detects whether the eye to be examined is the left eye or the right eye by detecting the relational position of a base and the moving portion.

18. A method according to claim 15, further comprising the step of storing data representing the position at which the reference mark corresponding to the left eye or the right eye is displayed.

19. A method according to claim 15, wherein said guiding step comprises the step of presenting a fixation target to the eye to be examined, and further comprising the step of changing the position at which the fixation target is presented to the eye to be examined in accordance with the information detected by the left-right detecting means.

20. A method according to claim 15, wherein said guiding step comprises the step of presenting means for presenting a fixation target to the eye to be examined, and further comprising the step of adjusting the position of the fixation target.

21. A method for displaying a cornea of an eye to be examined comprising the steps of:

projecting a mark for alignment onto the cornea of the eye to be examined;

displaying a reference mark for permitting a reflected image of the mark to be positioned relative thereto;

detecting whether the eye to be examined is the left eye or the right eye;

displaying the mark for alignment and the reference mark; and changing the position at which the reference mark is displayed in accordance with a detection result obtained by said detecting step.

* * * * *